Figure 1:
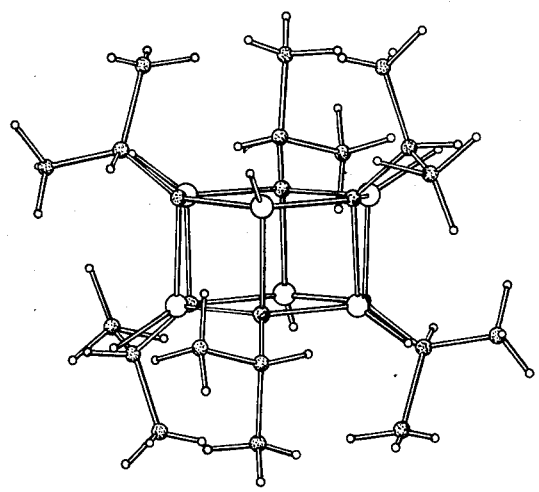

United States Patent [19]

Cucinella et al.

[11] 4,064,153

[45] Dec. 20, 1977

[54] OLIGOMER N-ALKYL-IMINOALANES AND PROCESS FOR THE PREPARATION THEREOF

[75] Inventors: Salvatore Cucinella; Marco Cesari; Tito Salvatori, all of San Donato Milanese, Italy

[73] Assignee: Snam Progetti S.p.A., Milan, Italy

[21] Appl. No.: 592,248

[22] Filed: July 1, 1975

[30] Foreign Application Priority Data

July 1, 1974 Italy ................................ 24663/74

[51] Int. Cl.$^2$ .............................................. C07L 5/06
[52] U.S. Cl. ............................ 260/448 R; 260/2 M
[58] Field of Search .......................... 260/448 R, 2 M

[56] References Cited

U.S. PATENT DOCUMENTS

| | | | |
|---|---|---|---|
| 3,245,976 | 4/1966 | Marconi et al. | 260/94.3 |
| 3,311,604 | 3/1967 | Marconi et al. | 260/94.3 |
| 3,505,246 | 4/1970 | Ehrlich et al. | 260/2 M |
| 3,781,318 | 12/1973 | Corbellini et al. | 260/448 R |

OTHER PUBLICATIONS

Ehrlich et al. (II) Inorg. Chem. 3 (1964) pp. 628–630.

*Primary Examiner*—Arthur P. Demers
*Attorney, Agent, or Firm*—Ralph M. Watson

[57] ABSTRACT

An oligomer N-alkyl-iminoalane, made up of a plurality of four and/or six member rings of the formulae:

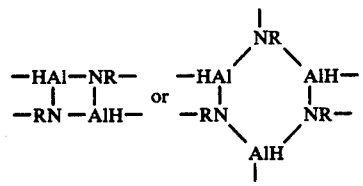

wherein R is an aliphatic, cycloaliphatic or aromatic hydrocarbon combined in a tridimensional cage structure having the chemical composition $(HAl-NR)_n$, in which R has the above meaning and n is a whole number lower than or equal to 10, is prepared by reacting a primary amine containing a secondary or tertiary carbon atom in alpha or beta position with respect to the amine nitrogen atom or amide derivative thereof wherein the amine radical contains a secondary or tertiary carbon atom in alpha or beta position with respect to the nitrogen atom with a complex formed by $AlH_3$ and a Lewis base, or by reacting said primary amine with an alkali or alkaline-earth metal alanate.

8 Claims, 2 Drawing Figures

OLIGOMER N-ALKYL-IMINOALANES AND PROCESS FOR THE PREPARATION THEREOF

The present invention relates to oligomer N-alkyl-imino-alanes having the chemical composition -(A1H-NR)-$_n$ in which R is an aliphatic, cycloaliphatic or aromatic hydrocarbon and n is a whole number lower than or equal to 10, constituted by a variety of four and/or six membered condensed rings of the type

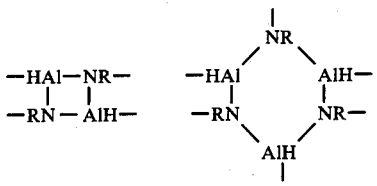

i.e., by structures in which such rings have (HAL - NR) unities in common.

These oligomers have therefore a "cage" tridimensional structure, show H$_{active}$/Al atomic ratios equal or practically equal to 1 and N/Al atomic ratios equal to 1, active hydrogen atoms being the hydride hydrogen atoms directly bound to aluminum, that can be analytically determined, for instance as hydrogen developed by reacting the inventive products, dissolved in inert solvents, which are high boiling alcohols or water.

Furthermore the present invention relates also to the methods for the preparation of the aforesaid compounds.

Polymeric aluminum derivatives are known as are as the methods for the preparation thereof.

In fact the reaction between ether-dioxane solutions of AlH$_3$ and methylamine has been reported by Wiberg and May in "Z. Naturforsch. 10 b 232 (1955)"; according to these authors there is obtained an insoluble substance to which has been assigned a polymeric structure corresponding to a poly (N-methyl-iminoalane) containing repeated unities of the type -Hal-NCH$_3$-.

More recently Ehrlich and May, in U.S. Pat. No. 3,505,246, reported the preparation of similar compounds, which they named poly (N-ethylalazenes) and poly (N-methylalazenes) and defined as long chain-polymeric compounds, having a polymerization degree of the (HAl-NR) unities of at least 10.

Moreover the assigned of this application owns an Italian Patent Application, no. 31857 filed an Nov. 29, 1973, (and the corresponding U.S. application, Ser. No. 524,312, filed Nov. 15, 1974) relating to the preparation of poly (N-alkyl-iminoalanes) by reacting alkali or alkaline-earth metal alanates with primary amines.

We have now found that, if use in made of a primary amine containing a secondary or tertiary carbon atom in alpha or beta position with respect to the amine nitrogen atom or amide derivative thereof wherein the amine radical contains a secondary or tertiary carbon atom in alpha or beta position with respect to the nitrogen atom, and the operating conditions are controlled as hereinafter described, it is possible to obtain N-alkyl-aminoalane oligomers having a closed cage tridimensional structure and, hence, a well defined polymerization degree together with a practically absolute purity, which can be employed as components of polymerization catalyst systems or for carrying out reductions of many organic substrates (see U.S. patent application, Ser. No. 592,249, filed July 1, 1975, owned by the assignee of this application)

The first aspect of the present invention is the preparation of N-alkyl-iminoalane oligomers as aforesaid which are a further aspect of the invention, starting from amines having a secondary or tertiary carbon atom in alpha or beta position with respect to the nitrogen atom.

Examples of amines employable in the preparation of the products of our invention are iso-propyl-amine, sec-butyl-amine, isobutyl-amine, tert-butyl-amine, cyclo-butyl-amine.

Interesting applications are also found when use is made of products obtained by substituting, either partially or completely, hydride hydrogens with different atoms or groups such as halogen atoms, amine, hydroxyl, alpoxy mercaptan groups that can be obtained, for instance, by reacting the products, aforesaid defined, above with controlled amounts of halide acids, metal halides, primary amines differing from the N-alkyl-iminoalanes, secondary amines, nitriles, water, alcohols, hydrogen sulphide, mercaptans, etc.

The use of amines other than those cited above does not permit obtaining oligomer N-alkyl-iminoalanes having an average molecular wight defined by a whole number; on the contrary the obtained product is constituted by mixtures of imine derivatives.

Therefore it is to be recognized that the nature of the amine is fundamental with respect to the degree of polymerization molecular structure and purity of the N-alkyl-iminealane and these differences affect the catalytic activity thereof, particularly in polymerization.

The cage structures, as noted above, can be obtained by subjecting the reaction mixture, for instance in ethyl ether, to a protracted boiling, for 20 or more hours, and, in the particular case of derivatives obtained from amines containing alkyl radicals with high steric hindrance such as, for instance, tert-butyl-amine, by replacing the reaction solvent with a solvent having a higher boiling point, for instance toluene, and subjecting the resulting solution to a prolonged boiling, or also by carrying out the reaction directly in a higher boiling solvent, at the boiling temperature thereof and, at the end, subjecting the reaction mixture thus obtained to boiling.

The process of our invention is preferably carried out through one of the following reactions:

1. AlH$_3$ . B + R-NH$_2$ → 1/n (AlHNR)$_n$ + 2H$_2$ °B
2. Al (NHR)$_3$ 2AlH$_3$ . B → 3/n (AlHNR)$_n$ + 3H$_2$ + B B = an organic Lewis base such as the ethers, trialkylamines, tetrahydrofuran, etc.
3. MAlH$_4$ + R -NH$_2$→1/n (AlHNR)$_n$ + MH + 2H$_2$ M = an akali or alkaline-earth metal.

The aforesaid reactions are carried out in hydrocarbon solvents in the presence of solvents having no functional group able to react with hydride hydrogens, at temperatures of from -20° C to the decomposition temperature of the obtained compound.

When use is made of a reaction between LiAlH$_4$ and a salt of a primary amine with a halide acid.

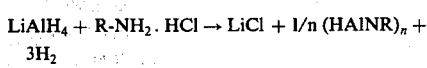

it is possible to obtain cage tridimensional structures as aforesaid when the reaction solution or the obtained product solution, preferably in solvents having a higher boiling point, are subjected to a protracted boiling, for instance for over 20 hours or more.

The operating procedures become clearer by examining the following illustrative examples, which are not to be construed as limiting the scope of our invention.

EXAMPLE 1

Under a nitrogen atmosphere, a solution, of by iso-propylamine (133 mmoles) in diethyl ether (40 ml) was added, dropuise, to a stirred solution of $AlH_3 \cdot N(CH_3)_3$ (133 mmoles) in diethyl ether (100 ml), at room temperature. Hydrogen developed at once. The reaction mixture was kept under stirring for 2 hours at room temperature, and was rested for 20 hours. Then the solvent and trimethylamine were removed through evaporation under vacuum. The white solid residue was again dissolved in diethyl ether (about 100 ml), the solution was filtered in order to eliminate small traces of insoluble material, then cooled at $-50°$ C. A precipitate formed which was separated through a filtration at $-50°$ C, dried (10 hours, room temperature, $10^{-3}$ mmHg) to give 6.4 g of product.

| Analysis | Al | N | $H_{act}/Al$ |
|---|---|---|---|
| Found | 30.67 % | 16.24 % | 1.01 |
| Calculated for $(HAlNC_3H_7)_6$ | 31.71 % | 16.46 % | 1 |

The remaining solution was evaporated under vacuum and the residual solid product was dried (10 hours, room temperature, $10^{-3}$ mmgH) to give 5.7 g of product.

| Analysis | Al | N | $H_{act}/Al$ |
|---|---|---|---|
| Found | 28.55 % | 15.97 % | 0.99 |
| Calculated for $(HAlNC_3H_7)_6$ | 31.71 % | 16.46 % | 1 |

Both the fraction separated at $-50°$ C and the solid obtained from the evaporation of the remaining solution were characterized by physical-chemical measurements. Particularly the molecular structure was determined by means of the X-ray difractometry on a single crystal obtained from the fraction separated at $-50°$ C.

A hexamer structure was found, in which Al and N atoms were bound to form a cage having ternary symmetry as illustrated in FIG. 1.

Other physical-chemical data confirmed the formation, practically the only one, of this product both in the fraction separated at $-50°$ C and in the residue from the evaporation of the resulting solution.

Particularly the mass spectrum showed a molecular ion M+· abundant at m/e 510, together with ions (M-H)+ at m/e 509 and (M-2H)+at m/e 508, and a prevailing ion at m/e 495 derived from the molecular ion through a methyl radical loss.

The $1_H$NMR spectrum, in benzene solution, showed a doublet at $\tau$ 8.49 and a sextet at $\tau$ 6.29 due to the protons of $CH_3$ and CH groups of amine radical; the spectrum agreed with symmetrical structure.

Furthermore molecular weight measurements, carried out in boiling ethyl ether solutions, showed values of 528 and 495for the two fractions, respectively, close to the value 510 calculated for $(HAlNisco-C_3H_7)_6$; the IR spectrum in nujol showed a maximum $\nu_{Al-H}$ at 1850 $cm^{-1}$ in agreement with the presence of tetracoordinated Al.

EXAMPLE 2

Under a nitrogen atmosphere, a solution of $AlH_3 \cdot$ THF (55.5 mmoles) in tetrahydrofuran (50 ml) was slowly added to a stirred solution of $iso\text{-}C_3H_7NH_2$ (55.5 mmoles) in tetrahydrofuran (50 ml).

At the end, after stirring at room temperature for 10 hours, the solution was partially evaporated to a volume of 50 ml, and kept at $-10°$ C for 50 hours. Crystals were separated, that were filtered, dried (10 hours room temperature, $10^{-3}$ mmHg) to give 1.9 g of product.

| Analysis | AL | N | $H_{act}/Al$ |
|---|---|---|---|
| Found | 30.54 % | 15.49 % | 1.05 |
| Calculated for $(HAlNC_3H_7)_6$ | 31.71 % | 16.46 % | 1 |

The physical-chemical determinations showed it to be hexa(N-isopropylaminoalane) having the structure illustrated in FIG. 1.

The remaining solution, completely evaporated, gave a white solid residue, which was still mainly constituted by hexa(N-isopropyliminoalane) together with complexes thereof with tetrahydrofuran and minimum amounts of different N-isopropyliminoalanes.

EXAMPLE 3

Under a nitrogen atmosphere, a solution formed by tert-butylamine (120 mmoles) in benzene (50 ml) was slowly added to a stirred suspension of $NaAlH_4$ (124 mmoles) in benzene (150 ml).

The whole was kept under stirring at the solvent reflux temperature and the increase of the Al/N ratio in solution; was followed analytically; when this was close to 1 (Al/N = 0.87), the reaction was hastened by adding a slight excess of $NaAlH_4$. At the end, at an Al/N molar ratio equal to 1, the reaction mixture was filtered.

From the solution the solvent was removed through evaporation under vacuum and the white solid residue was dried (10 hours room temperature, $10^{-3}$ mmH) to give g of 10 g product.

| Analysis | Al | N | $H_{act}/Al$ |
|---|---|---|---|
| Found | 26.21 % | 13.55 % | 0.98 |
| Calculated for $(AlHNC_4H_9)_4$ | 27.22 % | 14.13 % | 1 |

Figure 2:
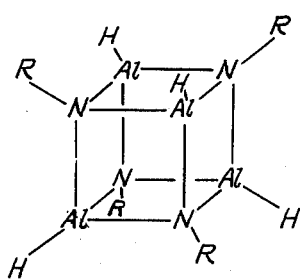

The physical-chemical determinations agreed with the formation of a tetramer as illustrated in FIG. 2.

The mass spectrometry showed very abundant ions $(M\text{-}CH_3)^+$ derived from tetramers at m/e 381.

The $1_H$NMR examination in benzene solution, showed one single signal due to the $CH_3$ protons at $\tau$ 8.56 in agrement with the structural equivalency of the four amine radicals.

The molecular weight, determined in boiling diethyl ether solution was 370, close to the calculated value of 396.5. The IR spectrum in nujol showed a band $\nu_{Al-H}$ with a maximum at 1860 $cm^{-1}$ in agreement with the presence of tetracoordinated Al.

EXAMPLE 4

According to the procedure described in Example 3, $LiAlH_4$(118.5 mmoles) was reacted with iso-butylamine (115 mmoles) in benzene (complexively 200 ml). The reaction was hastened by adding an excess of LiAlH$_4$ when Al/N = N 0.85.

At the end (Al/N ion solution equal to 1) the reaction mixture was filtered. From the solution the solvent was removed through under vacuum and the white solid residue was dried (10 hours, room temperature, $10^{-3}$ mmHg) to give g of product.

| Analysis | Al | N | H$_{act}$/Al |
|---|---|---|---|
| Found | 27.15 % | 13.79 % | 1.03 |
| Calculated for (HAlNC$_3$H$_7$)$_6$ | 27.22 % | 14.3 % | 1 |

The physical-chemical data confirmed the formation of hexa (N-iso-butyliminoalane).

The molecular weight, in boiling ethyl ether solution was 650, close to the calculated value of 594.7.

A (M-C$_3$H$_7$)$^+$ at m/e 551 prevailed in the mass spectrum agreeing with the formation of a hexamer

According to the structural equivalency of amine groups, the $1_H$NMR spectrum in benzene showed a doublet at $\tau$8.92, a multiplet at $\tau$7.96 and a doublet at $\tau$6.80 having a relative intensity 6 : 1 : 2, due to the protons of CH$_3$ CH and CH$_2$ respectively.

The IR spectrum, in nujol, showed a band $\nu$ Al-H at 1850 cm$^{-1}$, in agreement with the presence of tetracoordinated aluminium atoms.

EXAMPLE 5

13.53 ml of an ether solution of HCl, 0.72 M concentrated, were slowly added, under a magnetic stirring at room temperature to a solution formed by hexa (N-isopropyliminoalane) (57.3 mmoles of aluminium). At the end the whole was kept under stirring for 1 hour and was rested for 20 hours. Small amounts of insoluble material were filtered and the solution was under vacuum evaporated to give a white solid residue which was dried (10 hours, room temperature $10^{-3}$ mmHg) and analyzed.

| Analysis | Al | Cl | N | H$_{act}$ |
|---|---|---|---|---|
| Found | 27.15 % | 5.78 % | 15 % | 8.4 meq/g |
| Calculated for [(HAlNC$_3$H$_7$)$_5$ (ClAlHC$_3$H$_7$)$_1$] | 29.70 % | 6.50 % | 15.42 % | 9.17 meq/g |

The physical-chemical determinations (mass spectrometry, $1_H$NMR agreed with the formation of hexa (N-isopropyliminoalane), partially chlorinated, according to the aforesaid average composition.

EXAMPLE 6

10.4 ml of an ether solution of HCl, 0.72 M concentrated, were slowly added, under a magnetic stirring at room temperature, to a solution of tetra (n-tert-butyliminoalane) (30 mmoles of Al). At the end the whole was kept under stirring for 1 hour and rested for 20 hours. Small amounts of insoluble material were filtered and the solution was under vacuum evaporated to give a white solid residual that was dried (10 hours room temperature, $10^{-3}$ mmHg) and analyzed

| | Al | Cl | N | H$_{act}$ |
|---|---|---|---|---|
| Found | 24.65 % | 7.14 % | 13.13 % | 6.8 meq/g |
| Calculated for [(HAlNC$_4$H$_9$)$_3$ | | | | |

-continued

| | Al | Cl | N | H$_{act}$ |
|---|---|---|---|---|
| (ClAlHC$_4$H$_9$)$_1$] | 25.01 % | 8.24 % | 13.03 % | 6.97 meq/g |

The physical-chemical determinations (mass spectrometry, $1_H$NMR) agreed with the formation of tetra (N-tert-butyliminoalane), partially chlorinated, according to the aforesaid average composition.

EXAMPLE 7

A solution of hexa (N-isopropyliminoalane) (86.8 mmoles) in heptane (150 ml) was slowly added to a solution of TiCl$_4$ (86.8 mmoles) in heptane (150 ml) at room temperature. The reaction was accompanied by gas development and a formation of a dark precipitate At the end a filtration was carried out, the precipitate was repeatedly washed with heptane, dried and analyzed.

It consisted of a mixture of $\beta$-TiCl$_3$ and oligomer (N-isopropylchlorominoalane) having a composition, as shown by mass spectrometry measurements (ClAl-NC$_3$H$_7$)$_6$ This was extracted by subjecting the reaction product to a prolonged extraction with boiling benzene, in which TiCl$_3$ is insoluble. (N-isopropylchloroiminoalane) oligomer was quantitatively separated, in the form of white crystals, by cooling the benzene solution to room termperature.

It was recovered through a filtration, dried to give 8.7 g of crystallin product and analyzed

| | Al | N | Cl |
|---|---|---|---|
| Found | 21.73 % | 11.52 % | 29.41 % |
| Calculated for (ClAlNC$_3$H$_7$)$_6$ | 22.6 % | 11.70 % | 29.6% |

What we claim is:

1. An oligomer N-alkyl-iminoalane consisting of a plurality of four and/or six membered rings of the formula:

$$-HAl-NR- \quad \text{or} \quad \begin{array}{c} NR \\ HAl \quad AlH \\ RN \quad NR- \\ AlH \end{array}$$
$$-RN-AlH-$$

in which R is selected from the group consisting of iso-propyl, sec-butyl, iso-butyl, tert-butyl and cyclo-butyl, combined to form a tridimensional cage structure having the chemical composition (HAlNR)$_n$ in which R has the meaning given above, and n is a whole number lower than or equal to 10.

2. The process of preparing an oligomer N-alkyliminoanale as claimed in claim 1, which consists of reacting a primary amine selected from the group consisting of iso-propyl-amine, sec-butyl-amine, iso-butyl-amine, tert-butyl-amine, and cyclo-butyl-amine, with a complex formed by AlH$_3$ and a Lewis base.

3. The process of preparing an iminolane as claimed in claim 1, which consists in reacting an alkali alanate with a primary amine selected from the group consisting of iso-propyl-amine, sec-butyl-amine, iso-butyl-amine, tert-butyl-amine, and cyclo-butyl-amine.

4. The process of preparing an oligomer N-alkyl-iminoalane as claimed in claim 1 wherein the reaction is carried out in the presence of a member of the group consisting of the hydrocarbon solvents, ether solvents and solvents containing no functional group able to react with hydride hydrogen.

5. The process of preparing an oligomer N-alkyl-iminoalane as claimed in claim 1, wherein the reaction is carried out in the temperature range of from $-20°$ C to the dissociation temperature of said oligomer N-alkyl-iminolane.

6. The process of preparing an oligomer N-alkyl-iminoalane as claimed in claim 4, wherein the reaction is carried out at the boiling temperature of the solvent for a period of at least 20 hours.

7. The process of preparing an oligomer N-alkyl-iminoalane as claimed in claim 4, wherein the reaction is carried out by replacing the reaction solvent with a higher boiling solvent and heating the reaction mixture to the boiling temperature thereof for a period of at least 20 hours.

8. The process as claimed in claim 3, wherein the alkali alanate is $NaAlH_4$ or $LiAlH_4$.

* * * * *

UNITED STATES PATENT AND TRADEMARK OFFICE
CERTIFICATE OF CORRECTION

PATENT NO. : 4,064,153
DATED : December 20, 1977
INVENTOR(S) : Salvatore Cucinella, et al It is certified that error appears in the above-identified patent and that said Letters Patent are hereby corrected as shown below:

Column 1, line 21, Correct "(HAL-NR)" to read --(HA1-NR)--.

line 34, After "are" delete --as--.

line 49, Correct "assigned" to read --assignee--.

Column 2, line 19, Delete "aforesaid".

line 19, After "defined" delete the comma --,--.

line 20, After "above" insert a comma ",".

line 31, After "the" insert --resulting--.

line 32, Correct spelling of "iminoalane".

line 51, After "$2H_2$" delete the degree sign "°" and insert a plus symbol --+--.

line 52, Before "$2AlH_3$" insert a plus symbol -- + --.

line 64, After "acid" change the period "." to a colon --:--.

UNITED STATES PATENT AND TRADEMARK OFFICE
CERTIFICATE OF CORRECTION

PATENT NO. : 4,064,153
DATED : December 20, 1977
INVENTOR(S) : Salvatore Cucinella, et al It is certified that error appears in the above-identified patent and that said Letters Patent are hereby corrected as shown below:

Column 3, line 5, Delete "over".

line 6, After "procedures" insert --will--.

line 11, After "solution" delete the comma ",".

line 11, Delete "by".

line 13, Correct spelling of "dropwise".

line 34, Correct "mmgH" to read --mmHg--.

Column 4, line 37, After "solution" delete the semi-colon ";".

line 43, Correct "mmH" to read --mmHg--.

line 44, Correct "g of 10g" to read --10g of--.

Column 5, line 6, After "through" insert --evaporation--.

line 6, After "vacuum" insert a comma --,--.

line 8, Before "g" insert --7--.

UNITED STATES PATENT AND TRADEMARK OFFICE
CERTIFICATE OF CORRECTION

PATENT NO. : 4,064,153
DATED : December 20, 1977
INVENTOR(S) : Salvatore Cucinella, et al It is certified that error appears in the above-identified patent and that said Letters Patent are hereby corrected as shown below:

Column 5, line 13, Under heading "N", second line, Correct "14.3%" to read --14.13%--.

line 25, After "$CH_3$" insert a comma --,--.

line 34, After "temperature" insert a comma --,--.

line 38, After "was" insert --evaporated--.

line 39, Before "to" delete "evaporated".

line 40, After "temperature" insert a comma --,--.

line 50, After "$1_H NMR$" close the parenthesis --)--.

line 61, After "was" delete "under vacuum" and after evaporated" insert --under vacuum--.

line 62, Correct "residual" to read --residue--.

UNITED STATES PATENT AND TRADEMARK OFFICE
CERTIFICATE OF CORRECTION

PATENT NO. : 4,064,153
DATED : December 20, 1977
INVENTOR(S) : Salvatore Cucinella, et al It is certified that error appears in the above-identified patent and that said Letters Patent are hereby corrected as shown below:

Column 6, line 16, Before "formation" delete --a-- and after "precipitate" insert a period --.--.

line 24, Correct the line to read

--(ClAl-NC$_3$H$_7$)$_6$--.

line 62, Correct spelling of "alkyliminoalane".

line 62, After "consists" correct "of" to read --in--.

Signed and Sealed this

Eleventh Day of July 1978

[SEAL]

Attest:

RUTH C. MASON
Attesting Officer

DONALD W. BANNER
Commissioner of Patents and Trademarks